United States Patent [19]

Foster et al.

[11] Patent Number: 5,073,609

[45] Date of Patent: * Dec. 17, 1991

[54] DNA SEQUENCE CODING FOR PROTEIN C

[75] Inventors: Donald C. Foster, Seattle; Earl W. Davie, Bellevue, both of Wash.

[73] Assignee: The Board of Regents of the University of Washington, Seattle, Wash.

[*] Notice: The portion of the term of this patent subsequent to Nov. 6, 2007 has been disclaimed.

[21] Appl. No.: 375,260

[22] Filed: Jun. 29, 1989

Related U.S. Application Data

[62] Division of Ser. No. 766,109, Aug. 15, 1985, Pat. No. 4,968,626.

[51] Int. Cl.$^5$ ............................................. C07H 15/12
[52] U.S. Cl. ...................................................... 536/27
[58] Field of Search ................ 536/27; 435/172.3, 226; 935/14

[56] References Cited

U.S. PATENT DOCUMENTS

| | | | |
|---|---|---|---|
| 4,775,624 | 10/1988 | Bang et al. | 435/236 |
| 4,784,950 | 11/1988 | Hagen et al. | 435/69.1 |
| 4,968,626 | 11/1990 | Foster et al. | 435/320.1 |

FOREIGN PATENT DOCUMENTS

| | | |
|---|---|---|
| 138222 | 4/1985 | European Pat. Off. |
| WO85/00521 | 2/1985 | PCT Int'l Appl. |

OTHER PUBLICATIONS

J. H. Griffin et al., "Deficiency of Protein C in Congenital Thrombotic Diseases", *J. Clin. Invest.* 68:1370–1373, 1981.

W. Kisiel, "Human Plasma Protein C", *J. Clin. Invest.* 64:761–769, 1979.

V. W. M. van Hisbergh et al., "Activated Protein C Decreases Plasminogen Activator-Inhibitor Activity in Endothelial Cell-Conditioned Medium", *Blood* 65:444–451, Feb. 1985.

W. Kisiel et al., "Enzymological Aspect of Blood Coagulation", *Behring Inst. Mitt.* 73:29–42, 1983.

J. E. Gardiner and J. H. Griffin, "Human Protein C and Thromboembolic Disease", *Progress in Hematology*, 265–278, 1983.

Philip C. Comp et al., "Generation of Fibrinolytic Activity by Infusion of Activated Protein C into Dogs", *J. Clin. Invest.* 68:1221–1228, 1981.

Y. Sakata et al., "Activated Protein C Stimulates the Fibrinolytic Activity of Cultured Endothelial Cells and Diseases Antiactivator Activity", *Proc. Acad. Sci. USA* 82:1121–1125, 1985.

A. Broekmans et al., "Congenital Protein C Deficiency and Venous Thromboembolism", *The New England Journal of Medicine* 309:340–344, 1983.

U. Seligsohn et al., "Homozygous Protein C Deficiency Manifested by Massive Venous Thrombosis in the Newborn", *The New England Journal of Medicine* 310:559–562, 1964.

R. A. Marlar, "Mechanism of Action of Human Activated Protein C, a Thrombin-Dependent Anticoagulant Enzyme", *Blood* 59:1067–1072, 1982.

Kisiel and Davie, "Protein C", *Methods in Enzymology* 80:320–332, 1981.

Miletich and Broze, "Characterization of Monoclonal Antibody Specific for the Heavy Chain of Non-Activated Human Protein C", *Thrombosis* 305a:1123, Nov. 1983.

Esmon et al., "Identification of an Encothelial Cell Cofactor for Thrombin-Catalyzed Activation of Protein C", *Proc. Natl. Acad. Sci.* (USA) 78:2249–2252, 1981.

(List continued on next page.)

*Primary Examiner*—Richard A. Schwartz
*Assistant Examiner*—Dian Cook
*Attorney, Agent, or Firm*—Seed and Berry

[57] ABSTRACT

Genomic and cDNA sequences coding for a protein having substantially the same biological activity as human protein C are disclosed. Recombinant plasmids and bacteriophage transfer vectors incorporating these sequences are also disclosed.

2 Claims, 9 Drawing Sheets

OTHER PUBLICATIONS

Kisiel et al., "Anticoagulant Properties of Bovine Plasma Protein C Following Activation by Thrombin", *Biochem.* 16:5824-5831, 1977.

Long et al., "Cloning and Sequencing of Liver cDNA Coding for Bovine Protein C", *Proc. Natl. Acad. Sci.* (USA) 81:5653-5656, 1984.

Walker et al., "The Inhibition of Blood Coagulation by Activated Protein C through the Selective Inactivation of Activated Factor V", *Biochim. et Biophys. Acta* 571:333-342, 1979.

Katayama et al., "Comparison of Amino Acid Sequence of Bovine Coagulation Factor IX (Christman Factor) with that of Other Vitamin K-Dependent Plasma Proteins", *Proc. Natl. Acad. Sci.* (USA) 76:4990-4994, 1979.

Kaufman and Sharp, "Construction of a Modular Dihydrofolate Reductase cDNA Gene: Analysis of Signals Utilized for Efficient Expression", *Mol. and Cell. Biol.* 2:1304-1319, 1982.

Kaufman, "Identification of the Components Necessary for Adenovirus Translational Control and their Utilization in cDNA Expression Vectors", *Proc. Natl. Acad. Sci* (USA) 82:689-693, 1985.

Hermonat et al., "Use of Adeno-Associated Virus as a Mammalian DNA Cloning Vector: Transduction of Neomycin Resistance into Mammalian Tissue Culture Cells", *Proc. Natl. Acad. Sci.* (USA) 81:6466-6470, 1984.

McMullen et al., "The Occurrence of -Hydroxyaspartic Acid in the Vitamin K-Dependent Blood Coagulation Zymogens", *Biochem. and Biophys. Res. Comm.* 115:8-14, 1983.

Ginsburg et al., "Human von Willebrand Factor (vWF): Isolation of Complementary DNA (cDNA) Clones and Chromosomal Localization", *Science* 228:1401-1406, 1985.

```
Ile Val Pro Ile Cys Leu Pro Asp Ser Gly Leu Ala Glu Arg Glu Leu Asn Gln Ala Gly Gln Glu Thr Leu Val Thr Gly Trp Gly Tyr His Ser Ser Arg Glu
ATA GTG CCC ATC TGC CTC CCG GAC AGC GGC CTT GCA GAG CGC GAG CTC AAT CAG GCC GGC CAG GAG ACC CTC GTG ACG GGC TGG GGC TAC CAC AGC AGC CGA GAG    8636

Lys Glu Ala Lys Arg Asn Arg Thr Phe Val Leu Asn Phe Ile Lys Ile Pro Val Val Pro His Asn Glu Cys Ser Glu Val Met Ser Asn Met Val Ser Glu Asn
AAG GAG GCC AAG AGA AAC CGC ACC TTC GTC CTC AAC TTC ATC AAG ATT CCC GTG GTC CCG CAC AAT GAG TGC AGC GAG GTG ATG AGC AAC ATG GTG TCT GAG AAC    8741

Met Leu Cys Ala Gly Ile Leu Gly Asp Arg Gln Asp Ala Cys Glu Gly Asp Ser Gly Gly Pro Met Val Ser Phe His Gly Thr Trp Phe Leu Val Gly Leu
ATG CTG TGT GCG GGC ATC CTC GGG GAC CGG CAG GAT GCC TGC GAG GGC GAC AGT GGG GGC CCC ATG GTC TCC TTC CAC GGC ACC TGG TTC CTG GTG GGC CTG        8846

Val Ser Trp Gly Glu Gly Cys Gly Leu Leu His Asn Tyr Gly Val Tyr Thr Lys Val Ser Arg Tyr Leu Asp Trp Ile His Gly His Ile Arg Asp Lys Glu Ala
GTG AGC TGG GGT GAG GGC TGT GGC CTC CTT CAC AAC TAC GGC GTT TAC ACC AAA GTC AGC CGC TAC CTC GAC TGG ATC CAT GGG CAC ATC AGA GAC AAG GAA GCC    8951

Pro Gln Lys Ser Trp Ala Pro STOP
CCC CAG AAG AGC TGG GCA CCT TAG    CGACCCTCC TGCAGGGCTG GGCTTTTGCA TGGCAATGGA TGGGACATTA AGGGACACAT TACAAGCGAC ACCGGCCTGC TGTCTGTCC TTCCATCCCT    9075
     419
CTTTGGGCT CTTCTGGCAG GAAGTAACAT TTACTGAGCA CCTGTGTGTAT GTCACATGCC TTATGAATAG AATCTTAACT CCTAGAGCAA CTCTGTGGGG TGGGAGGAG CAGATCCAAG TTTTGCGGGG    9205

TCTAAAGCTG TGTGTGTTGA CTTTCCAGGT GGGGATACT CTGTTTATGA AAAGAATAA AAACACAAC CACGAAGCCA CTAGAGCCTT TTCCAGGGCT TTGGAAGAG CCTGTGCAAG CCGGGATGC TGAAGGTGAG    9335

GCTTGACCAG CTTTCCAGT AGCCAGGCTA TGAGGTAGAC ATGTTTAGCT CATATCACAG AGGAGGAAAC TGAGGTGTCT GAAAGGTTTA CATGGTAGGA CCAGATTCA AATCTAGGTC TGACTCCAAA    9465
ACCAGGTGC TTTTTCTGT TCTCCACTGT CCTGGAGGAC AGCTGTTCG ACGGTGCTCA GTGTGAGGC CACTATTAGC TCTGTAGGA AGCAGCCAGA GACCCAGAGA GTGTGGTTC AGCCCAGAAT    9595
```

```
                                                                          -42   -40                                                          -30
                                                                          Met Trp Gln Leu Thr Ser Leu Leu Leu Phe Val Ala Thr
CGC CCA ACT TCC AGT ATC TCC ACC ACC CCC TCT CCC ACT CCC TCC AGA ATC TCC CAC CTC ACA ATC TCC CTC CTC TTC GTC GCC ACC              39

-20                                                      -10                                                    -1  +1
Trp Gly Ile Ser Gly Thr Pro Ala Pro Leu Asp Ser Val Phe Ser Ser Ser Glu Arg Ala His Gln Val Leu Glu Arg Ile Arg Lys Arg Ala
TGG GGA ATT TCC GGA ACA CCA GCT CCT CTT GAC TCA GTC TTC TCC AGC ACC GAG CGG GCC CAG GTG CTG GAG CGG ATC CGG AAA CGT GCC        129

10                                                      20                                                      30
Asn Ser Phe Leu Glu Glu Leu Arg His Ser Ser Leu Glu Arg Glu Cys Ile Glu Glu Ile Cys Asp Phe Glu Glu Ala Lys Glu Ile Phe
AAC TCC TTC CTC GAG GAG CTC CGT CAC AGC AGC CTC GAG CGG GAG TGC ATA GAG GAG ATC TGT GAC TTC GAG GAG GCC AAG GAA ATT TTC        219

40                                                      50                                                      60
Gln Asn Val Asp Asp Thr Leu Ala Phe Trp Ser Lys His Val Asp Gly Asp Gln Cys Leu Val Leu Pro Leu His Pro Cys Ala Ser
CAA AAT GTG GAT GAC ACA CTC GCT TTC TGG TCC AAG CAC GTC GAC GGG GAC CAG TGC CTG GTC CTG CCC TTC CAC CCC TGC GCC AGC            309

70                                                      80                                                      90
Leu Cys Cys Gly His Gly Thr Cys Ile Asp Gly Ile Gly Ser Phe Ser Cys Asp Cys Arg Ser Gly Trp Glu Gly Arg Phe Cys Gln Arg
CTC TGC TGC GGC CAC GGC ACC TGC ATC GAC GGC ATC GGC AGC TTC AGC TGC GAC TGC CGC AGC GGC TGG GAG GGC CGG TTC TGC CAG CGC        399

100                                                     110                                                     120
Glu Val Ser Phe Leu Asn Cys Ser Leu Asp Asn Gly Gly Cys Thr His Tyr Cys Leu Glu Glu Val Gly Trp Arg Arg Cys Ser Cys Ala
GAG GTC AGC TTC CTC AAT TGC TCT CTG GAC AAC GGC GGC TGC ACG CAT TAC TGC CTA GAG GAG GTG GGC TGG CGG CGC TGC AGC TGC GCC        489

130                                                     140                                                     150
Pro Gly Tyr Lys Leu Gly Asp Asp Leu Leu Gln Cys His Pro Ala Val Lys Phe Pro Cys Gly Arg Pro Trp Lys Arg Met Glu Lys Lys
CCT GGC TAC AAG CTC GGG GAC GAC CTC CTG CAG TGC CAT CCC GCC GTA AAG TTC CCT TGT GGG AGG CCC TGG AAG CGC ATG GAG AAG AAG        579

160                         170                                                     180
Arg Ser His Leu Lys Arg Asp Thr Glu Asp Gln Glu Asp Gln Val Asp Pro Arg Leu Ile Asp Gly Lys Met Thr Arg Arg Gly Asp Ser
CGC AGT CAT CTA AAA CGA GAC ACA GAA GAC CAA GAA GAC CAA GTA GAT CCG CGG CTC ATT GAT GGG AAG ATG ACC AGG CGG GGC GAC AGC        669
```

```
                                                190                          200                                   210
Pro Trp Gln Val Val Leu Leu Asp Ser Lys Lys Leu Ala Cys Gly Ala Val Leu Ile His Pro Ser Trp Val Leu Thr Ala His
CCC TGG CAG GTG GTC CTC CTG GAC TCA AAG AAG CTC GCC TGC GGA GCA GTC CTC ATC CAC CCC TCC TGG GTG CTC ACA GCC CAC   759

220                                  230                                   240
Cys Met Asp Glu Ser Lys Lys Leu Leu Val Arg Leu Gly Glu Tyr Asp Leu Arg Trp Glu Lys Trp Arg Trp Glu Leu Asp Leu Ile Lys
TGC ATG GAC GAG TCC AAG AAG CTC CTT GTC AGG CTT GGA GAG TAT GAC CTT CGA GCC CGG TGG GAG AAG TGG CGC TGG GAG CTG GAC CTC CAC ATC AAG   849

250                                    260                                    270
Glu Val Phe Val His Pro Asn Tyr Ser Lys Ser Thr Thr Asp Asn Asp Ile Ala Leu Leu His Leu Ala Gln Pro Ala Thr Leu Ser Gln
GAG GTC TTC GTC CAC CCC AAC TAC AGC AAG AGC ACC ACC GAC AAT GAC ATC GCA CTG CTC CAC CTC GCC CAG CCC GCC ACC CTC TCC CAG   939

280                                    290                                   300
Thr Ile Val Pro Ile Cys Leu Pro Asp Ser Gly Leu Ala Glu Arg Glu Leu Asn Gln Ala Gly Gln Glu Thr Leu Val Thr Gly Trp Gly
ACC ATA GTC CCC ATC TGC CTC CCC GAC AGC GGC CTT GCA GAG CGC GAG CTC AAT CAG GCC GGC CAG GAG ACC CTC GTG ACG GGG TGG GGC   1029

320                                    330
Tyr His Ser Ser Arg Glu Lys Glu Ala Lys Arg Asn Arg Thr Phe Val Leu Asn Phe Ile Lys Ile Pro Val Val Pro His Asn Glu Cys
TAC CAC AGC AGC CGA GAG AAG GAG GCC AAG AGA AAC AGG ACC TTC GTC CTC AAC TTC ATC AAG ATT CCC GTG GTC CCC CAC AAT GAG TGC   1119

340                                    350                                   360
Ser Glu Val Met Ser Asn Met Val Ser Glu Asn Met Leu Cys Ala Gly Ile Leu Gly Asp Arg Gln Asp Ala Cys Glu Gly Asp Ser Gly
AGC GAG GTC ATG AGC AAC ATG GTG TCT CAG AAC ATG CTC TGT GCT GGC ATC CTC GGG GAC CGG CAG GAT GCC TGC GAG GGC GAC AGT GGG   1209

370                                    380                                   390
Gly Pro Met Val Ala Ser Phe His Gly Thr Trp Phe Leu Val Gly Leu Val Ser Trp Gly Glu Gly Cys Gly Leu Leu His Asn Tyr Gly
GGG CCC ATG GTC GCC TCC TTC CAC GGC ACC TGG TTC CTC GTC GGC CTT GTG AGC TGG GGC GAG GGC TGT GGG CTC CTT CAC AAC TAC GGC   1299

400                                   410                                    419
Val Tyr Thr Lys Val Ser Arg Tyr Leu Asp Trp Ile His Gly His Ile Arg Asp Lys Glu Ala Pro Gln Lys Ser Trp Ala Pro STOP
GTT TAC ACC AAA GTC AGC CGC TAC CTC GAC TGG ATC CAT GGG CAC ATC AGA GAC AAG GAA GCC CCC CAG AAG AGC TGG GCA CCT TAC CGA   1389
```

FIG.3 CONT.

CCC TCC CTG CAG GCC TGG GCT TTT GCA TCC CAA TGG ATG GCA [CAT TAA A]GG CAC ATG TAA CAA GCA CAC CGG CCT GCT GTT CTC TCC TTC 1479

CAT CCC TCT TTT GGG CTC TTC TCG AGG GAA CTA ACA TTT ACT GAG CAC CTG TTC TAT GTC ACA TCC CTT ATG AAT AGA ATC TTA ACT CCT 1569

AGA GCA ACT CTG TCG GGT GGG CAG GAG CAG ATC CAA GTT TTC CGG GGT CTA AAG CTC TGT GTC TTC AGG CGG ATA CTC TGT TTA TGA AAA 1659

[AGA ATA AA]A AAC ACA ACC ACG AAA AAA AAA 3'   1689

FIG. 3 CONT.

DNA SEQUENCE CODING FOR PROTEIN C

CROSS-REFERENCE TO RELATED APPLICATION

This application is a division of U.S. patent application Ser. No. 06/766,109, filed Aug. 15, 1985, issued Nov. 6, 1990 as U.S. Pat. No. 4,968,626.

TECHNICAL FIELD

The present invention relates to sequences coding for plasma proteins in general and, more specifically, to a DNA sequence which codes for a protein having substantially the same structure and/or activity of human protein C.

BACKGROUND ART

Protein C is a zymogen, or precursor, of a serine protease which plays an important role in the regulation of blood coagulation and generation of fibrinolytic activity in vivo. It is synthesized in the liver as a single-chain polypeptide which undergoes considerable processing to give rise to a two-chain molecule comprising heavy (Mr = 40,000) and light (Mr = 21,000) chains held together by disulphide bonds. The circulating two-chain intermediate is converted to the biologically active form of the molecule, known as "activated protein C" (APC), by the thrombin-mediated cleavage of a 12-residue peptide from the amino-terminus of the heavy chain. The cleavage reaction is augmented in vivo by thrombomodulin, an endothelial cell cofactor (Esmon and Owen, *Proc. Natl. Acad. Sci. USA* 78: 2249-2252, 1981).

Protein C is a vitamin K-dependent glycoprotein which contains approximately eleven residues of gammacarboxyglutamic acid (gla) and one equivalent of betahydroxyaspartic acid which are formed by post-translational modifications of glutamic acid and aspartic acid residues, respectively. The post-translational formation of specific gamma-carboxyglutamic acid residues in protein C requires vitamin K. These unusual amino acid residues bind to calcium ions and are believed to be responsible for the interaction of the protein with phospholipid, which is required for the anticoagulant activity of protein C.

In contrast to the coagulation-promoting action of other vitamin K-dependent plasma proteins, such as factor VII, factor IX, and factor X, activated protein C acts as a regulator of the coagulation process through the inactivation of factor Va and factor VIIIa by limited proteolysis. The inactivation of factors Va and VIIIa by protein C is dependent upon the presence of acidic phospholipids and calcium ions. Protein S has been reported to regulate this activity by accelerating the APC-catalyzed proteolysis of factor Va (Walker, *J. Biol. Chem.* 255: 5521-5524, 1980).

Protein C has also been implicated in the action of plasminogen activator (Kisiel and Fujikawa, *Behring Inst. Mitt.* 73: 29-42, 1983). Infusion of bovine APC into dogs results in increased plasminogen activator activity (Comp and Esmon, *J. Clin. Invest.* 68: 1221-1228, 1981). Recent studies (Sakata et al., *Proc. Natl. Acad. Sci. USA* 82: 1121-1125, 1985) have shown that addition of APC to cultured endothelial cells leads to a rapid, dose-dependent increase in fibrinolytic activity in the conditioned media, reflecting increases in the activity of both urokinase-related and tissue-type plasminogen activators by the cells. APC treatment also results in a dose-dependent decrease in antiactivator activity.

Inherited protein C deficiency is associated with recurrent thrombotic disease (Broekmans et al., *New Eng. J. Med.* 309: 340-344, 1983; and Seligsohn et al., *New Eng. J. Med.* 310: 559-562, 1984) and may result from genetic disorder or from trauma, such as liver disease or surgery. This condition is generally treated with oral anticoagulants. Beneficial effects have also been obtained through the infusion of protein C-containing normal plasma (see Gardiner and Griffin in *Prog. in Hematology*, ed. Brown, Grune & Stratton, NY, 13: 265-278). In addition, some investigators have discovered that the anti-coagulant activity of protein C is useful in treating thrombotic disorders, such as venous thrombosis (WO 85/00521). In some parts of the world, it is estimated that approximately 1 in 16,000 individuals exhibit protein C deficiency. Further, a total deficiency in protein C is fatal in newborns.

While natural protein C may be purified from clotting factor concentrates (Marlar et al., *Blood* 59: 1067-1072) or from plasma (Kisiel, ibid), it is a complex and expensive process, in part due to the limited availability of the starting material and the low concentration of protein C in plasma. Furthermore, the therapeutic use of products derived from human blood carries the risk of disease transmission by, for example, hepatitis virus, cytomegalovirus, or the causative agent of acquired immune deficiency syndrome (AIDS). In view of protein C's clinical applicability in the treatment of thrombotic disorders, the production of useful quantities of protein C and activated protein C is clearly invaluable.

DISCLOSURE OF INVENTION

Briefly stated, the present invention discloses a DNA sequence which codes for a protein having substantially the same biological activity as human protein C.

In addition, the present invention discloses a recombinant plasmid or bacteriophage transfer vector comprising a cDNA sequence comprising the protein C gene cDNA sequence. The amino acid and DNA sequences of this cDNA coding for human protein C are also disclosed.

Other aspects of the invention will become evident upon reference to the detailed description and attached drawings.

BRIEF DESCRIPTION OF THE DRAWINGS

FIGS. 2 and 2A illustrates the complete genomic sequence, including exons and introns for human protein C. Arrowheads indicate intron-exon splice junctions. The polyadenylation or processing sequences of A-T-T-A-A-A and A-A-T-A-A-A at the 3' end are boxed.♦, potential carbohydrate binding sites; ↓ , apparent cleavage sites for processing of the connecting dipeptide; ↓ , site of cleavage in the heavy chain when protein C is converted to activated protein C; •, sites of polyadenylation.

FIG. 3 depicts the amino acid and DNA sequences for a cDNA coding for human protein C.

BEST MODE FOR CARRYING OUT THE INVENTION

Figure 1:
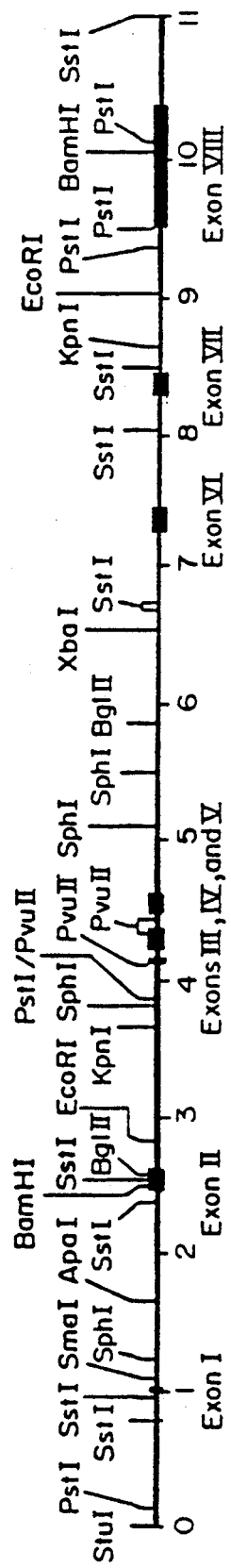
FIG. 1 illustrates a restriction enzyme map of the genomic DNA coding for human protein C.

Prior to setting forth the invention, it may be helpful to an understanding thereof to set forth definitions of certain terms to be used hereinafter.

Biological Activity: A function or set of functions performed by a molecule in a biological context (i.e., in an organism or an in vitro facsimile). Biological activities of proteins may be divided into catalytic and effector activities. Catalytic activities of the vitamin K-dependent plasma proteins generally involve the specific proteolytic cleavage of other plasma proteins, resulting in activation or deactivation of the substrate. Effector activities include specific binding of the biologically active molecule to calcium or other small molecules, to macromolecules, such as proteins, or to cells. Effector activity frequently augments, or is essential to, catalytic activity under physiological conditions.

For protein C, biological activity is characterized by its anticoagulant and fibrinolytic properties. Protein C, when activated, inactivates factor Va and factor VIIIa in the presence of phospholipid and calcium. Protein S appears to be involved in the regulation of this function (Walker, ibid). Activated protein C also enhances fibrinolysis, an effect believed to be mediated by the lowering of levels of plasminogen activator inhibitors (van Hinsbergh et al., Blood 65: 444–451, 1985). As more fully described below, Exons VII and VIII are primarily responsible for the catalytic activity of protein C.

Transfer Vector: A DNA molecule which contains, inter alia, genetic information which ensures its own replication when transferred to a host microorganism strain. Examples of transfer vectors commonly used for recombinant DNA are plasmids and certain bacteriophages. Transfer vectors normally include an origin of replication and sequences necessary for efficient transcription and translation of DNA.

As noted above, protein C is synthesized as a single-chain polypeptide which undergoes considerable processing to give rise to a two-chain molecule; a heavy chain ($M_r$ 41,000) and a light chain ($M_r$ 21,000), held together by a disulfide bond.

Within the present invention, a λgt11 cDNA library was prepared from human liver mRNA. This library was then screened with $^{125}$I labeled antibody to human protein C. Antibody-reactive clones were further analyzed for the synthesis of a fusion protein of B-galactosidase and protein C in the λgt11 vector.

One of the clones gave a strong signal with the antibody probe and was found to contain an insert of approximately 1400 bp. DNA sequence analysis of the DNA insert revealed a predicted amino acid sequence which shows a high degree of homology to major portions of the bovine protein C, as determined by Fernlund and Stenflo (J. Biol. Chem. 257: 12170–12179; J. Biol. Chem. 257: 12180–12190).

The DNA insert contained the majority of the coding region for protein C beginning with amino acid 65 of the light chain, including the entire heavy chain coding region, and proceeding to the termination codon. Further, following the stop codon of the heavy chain, there are 294 base pairs of 3' noncoding sequence and a poly (A) tail of 9 base pairs. The processing or polyadenylation signal A-A-T-A-A-A was present 13 base pairs upstream from the poly (A) tail in this cDNA insert. This sequence is one of two potential polyadenylation sites.

The cDNA sequence also contains the dipeptide Lys-Arg at position 156–157, which separates the light chain from the heavy chain and is removed during processing by proteolytic cleavage. Upon activation by thrombin, the heavy chain of human protein C is cleaved between arginine-12 and leucine-13, releasing the activation peptide.

In order to obtain the remainder of the light chain coding sequence (amino acids 1-64), a human genomic library in λ Charon 4A phage was screened for genomic clones of human protein C using the cDNA described above as a hybridization probe. Three different λ Charon 4A phage were isolated that contained overlapping inserts for the gene coding for protein C.

The position of exons on the three phage clones were determined by Southern blot hybridization of digests of these clones with probes made from the 1400 bp cDNA described above. The genomic DNA inserts in these clones were mapped by single and double restriction enzyme digestion followed by agarose gel electrophoresis, Southern blotting, and hybridization to radiolabeled 5' and 3' probes derived from the cDNA for human protein C, as shown in FIG. 1.

Figure 2:
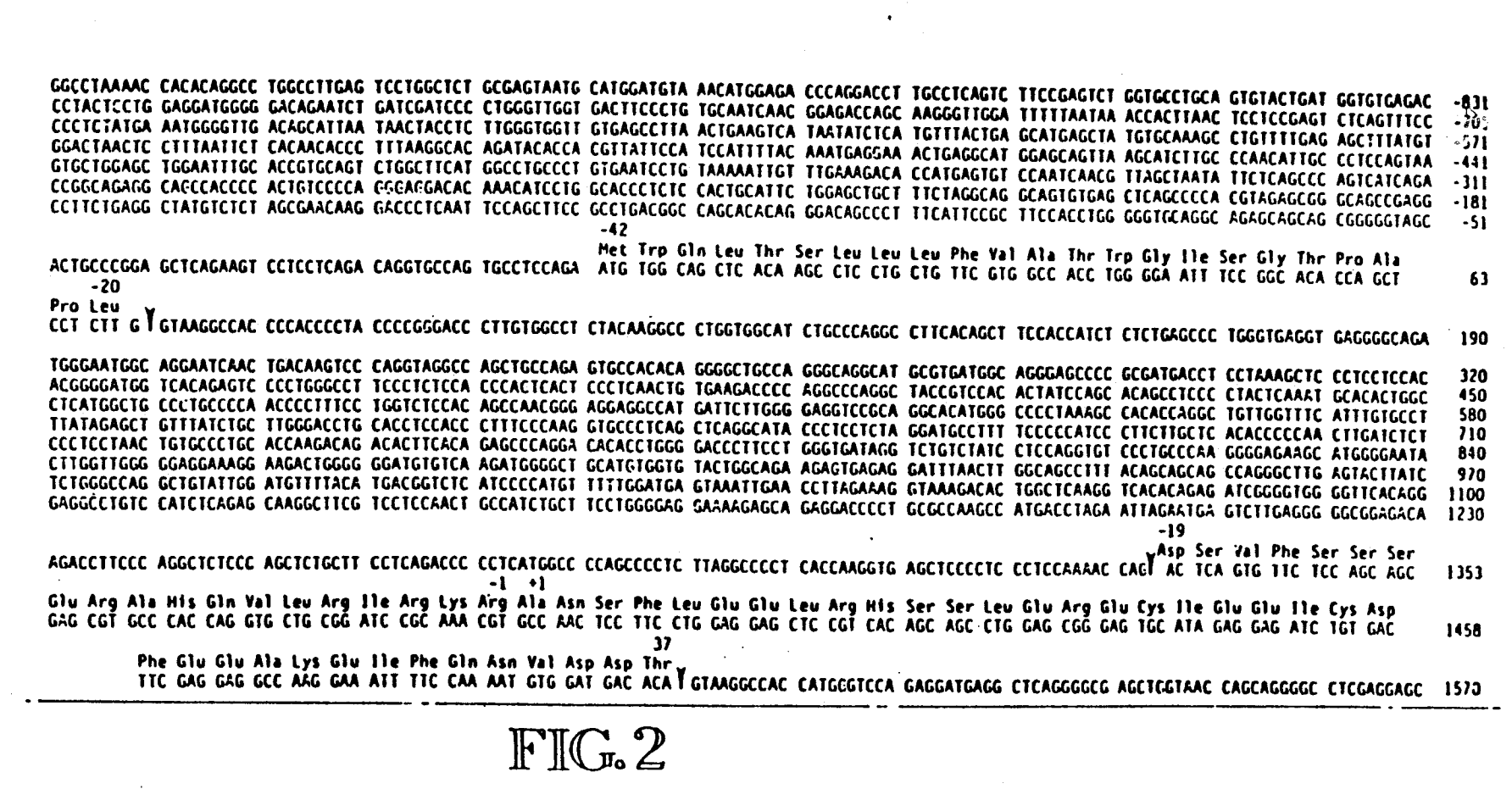
Figure 2:
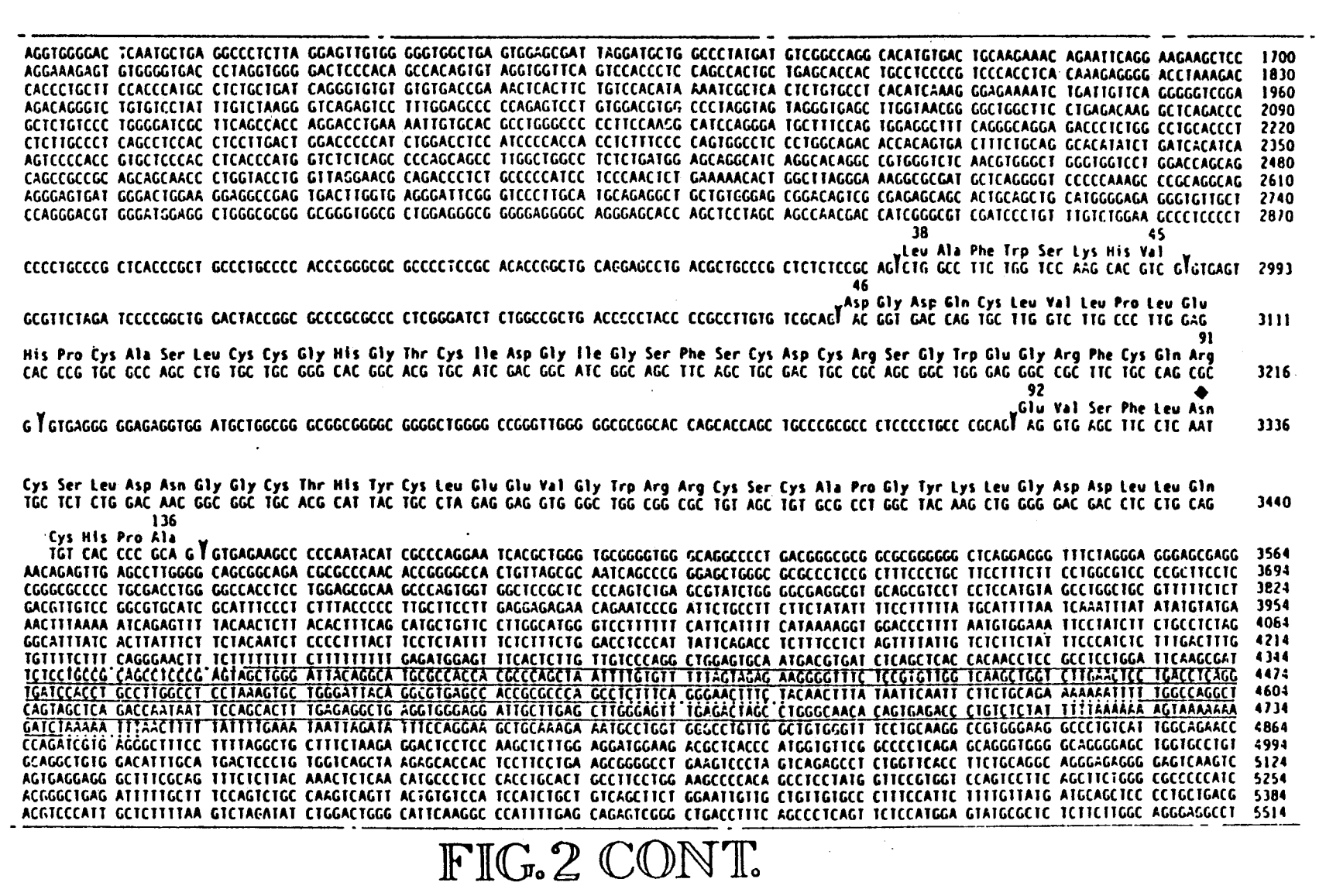
Figure 2:
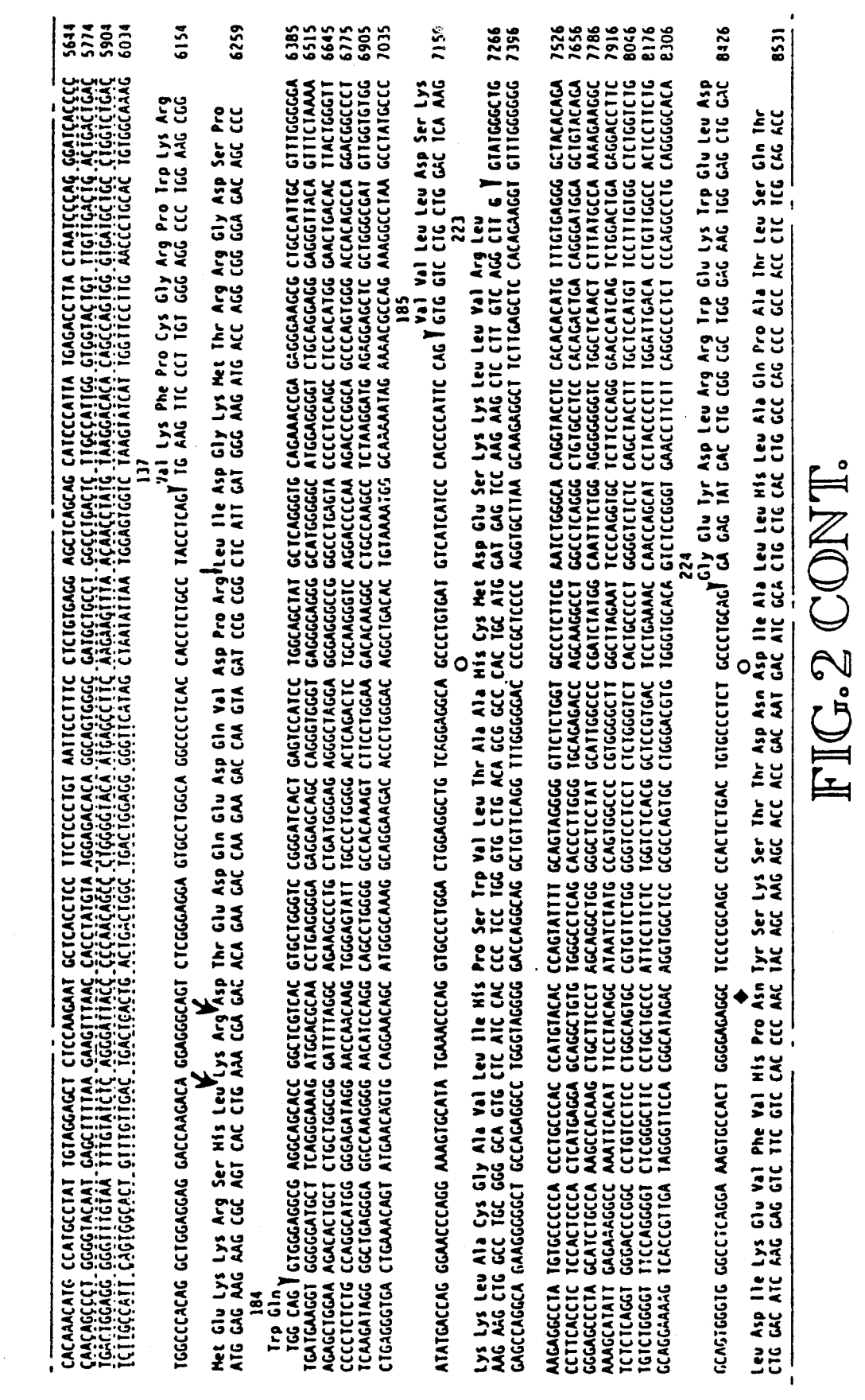

DNA sequencing studies were performed using the dideoxy chain-termination method. As shown in FIG. 2, the nucleotide sequence for the gene for human protein C spans approximately 11 kb of DNA. These studies further revealed a potential pre-pro leader sequence of 42 amino acids. Based on homology with the leader sequence of bovine protein C in the region −1 to −20, it is likely that the pre-pro leader sequence is cleaved by a signal peptidase following the Ala residue at position −10. Processing to the mature protein involves additional proteolytic cleavage following residue −1 to remove the amino-terminal propeptide, and at residues 155 and 157 to remove the Lys-Arg dipeptide which connects the light and heavy chains. This final processing yields a light chain of 155 amino acids and a heavy chain of 262 amino acids.

As noted above, the protein C gene is composed of eight exons ranging in size from 25 to 885 nucleotides, and seven introns ranging in size from 92 to 2668 nucleotides. Exon I and a portion of Exon II code for the 42 amino acid pre-pro peptide. The remaining portion of Exon II, Exon III, Exon IV, Exon V, and a portion of Exon VI code for the light chain of protein C. The remaining portion of Exon VI, Exon VII, and Exon VIII code for the heavy chain of protein C. The amino acid and DNA sequences for a cDNA coding for human protein C are shown in FIG. 3.

The location of the introns in the gene for protein C are primarily between various functional domains. Exon II spans the highly conserved region of the leader sequence and the gamma-carboxyglutamic acid (gla) domain. Exon III includes a stretch of eight amino acids which connect the Gla and growth factor domains. Exons IV and V each represent a potential growth factor domain, while Exon VI covers a connecting region which includes the activation peptide. Exons VII and VIII cover the catalytic domain typical of all serine proteases.

Figure 4:
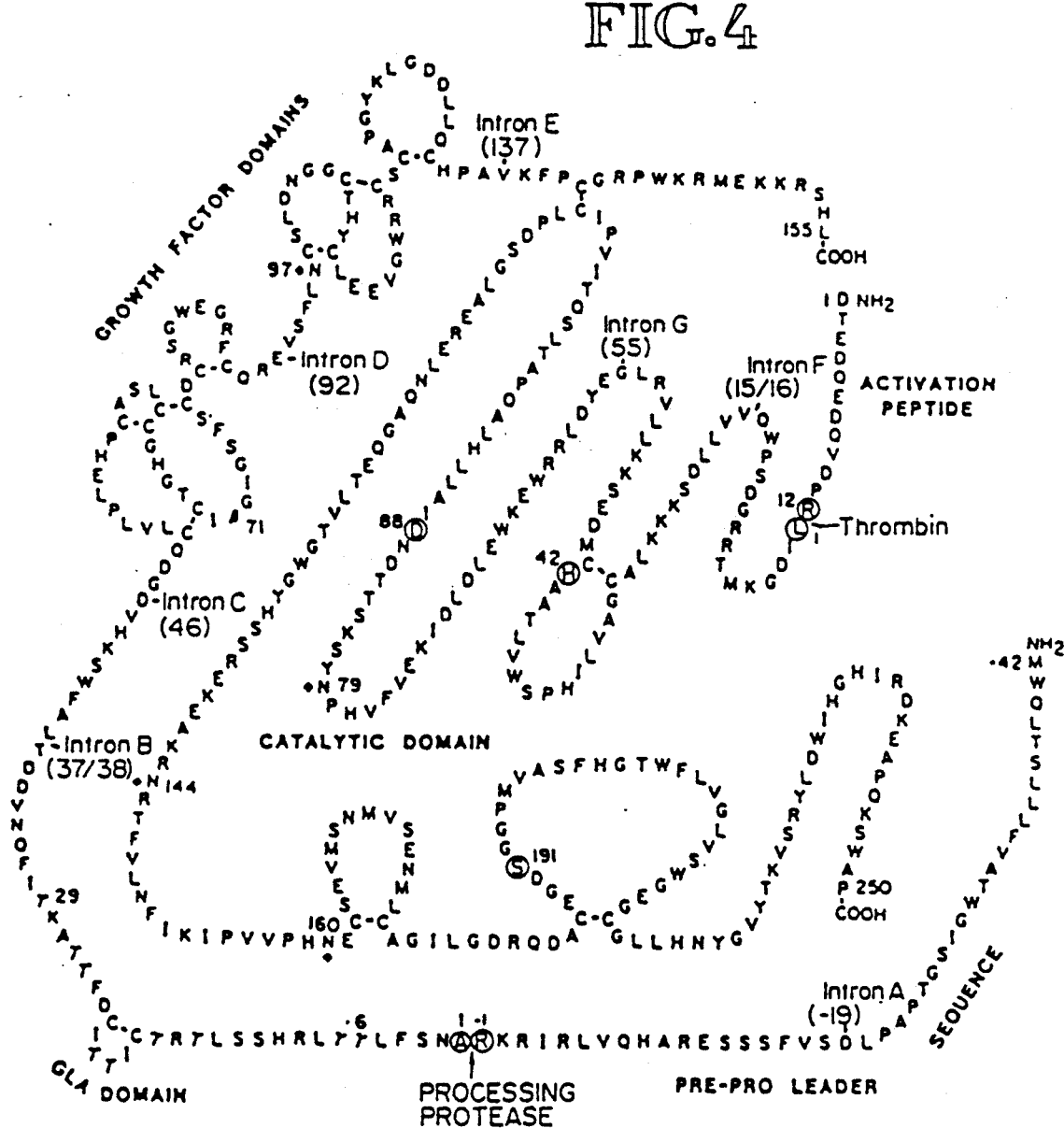
FIG. 4 illustrates a proposed model for the structure of human protein C.

The amino acid sequence and tentative structure for human pre-pro protein C are shown in FIG. 4. Protein C is shown without the Lys-Arg dipeptide, which connects the light and heavy chains. The location of the seven introns (A through G) is indicated by solid bars. Amino acids flanking known proteolytic cleavage sites are circled. ◆ designates potential carbohydrate binding sites. The first amino acid in the light chain, activation peptide, and heavy chain start with number 1, and differ from that shown in FIGS. 2 and 3.

Carbohydrate attachment sites are located at residue 97 in the light chain and residues 79, 144, and 160 in the heavy chain, according to the numbering scheme of FIG. 4. The carbohydrate moiety is covalently linked to Asn, but Thr, Ser, or Gln may be substituted. In the majority of instances, the carbohydrate attachment environment can be represented by N-X-Ser or N-X-Thr, where N = Asn, Thr, Ser, or Gln, and X = any amino acid.

The catalytic domain of protein C, which is encoded by Exons VII and VIII, plays a regulatory role in the coagulation process. This domain possesses serine protease activity which specifically cleaves certain plasma proteins (i.e., factors Va and VIIIa), resulting in their activation or deactivation. As a result of this selective proteolysis, protein C displays anticoagulant and fibrinolytic activities.

The example which follows describes the cloning of DNA sequences encoding human protein C.

EXAMPLE

Restriction endonucleases and other DNA modification enzymes (e.g., $T_4$ polynucleotide kinase, bacterial alkaline phosphatase, Klenow DNA polymerase, $T_4$ polynucleotide ligase) may be obtained from Bethesda Research Laboratories (BRL) and New England Biolabs and are used as directed by the manufacturer, unless otherwise noted.

Cloning of DNA Sequences Encoding Human Protein C

A cDNA coding for a portion of human protein C was prepared as described by Foster and Davie (PNAS (USA) 81: 4766-4770, 1984, herein incorporated by reference). Briefly, a λgt11 cDNA library was prepared from human liver mRNA by conventional methods. Clones were screened using $^{125}$I-labeled affinity-purified antibody to human protein C, and phage were prepared from positive clones by the plate lysate method (Maniatis et al., ibid), followed by banding on a cesium chloride gradient. The cDNA inserts were removed using Eco RI and subcloned into plasmid pUC9 (Vieira and Messing, Gene 19: 259-268, 1982). Restriction fragments were subcloned in the phage vectors M13mp10 and m13mp11 (Messing, Meth. in Enzymology 101: 20-77, 1983) and sequenced by the dideoxy method (Sanger et al., Proc. Natl. Acad. Sci. USA 74: 5463-5467, 1977). A clone was selected which contained DNA corresponding to the known sequence of human protein C (Kisiel, ibid) and encoded protein C beginning at amino acid 65 of the light chain and extending through the heavy chain and into the 3' non-coding region. This clone was designated λHC1375.

The cDNA insert from λHC1375 was nick translated using $\alpha$-$^{32}$P dNTP's and used to probe a human genomic library in phage λ Charon 4A (Maniatis et al., Cell 15: 687-702, 1978) using the plaque hybridization procedure of Benton and Davis (Science 196: 181-182, 1977) as modified by Woo (Meth. in Enzymology 68: 381-395, 1979). Positive clones were isolated and plaque-purified (by Foster et al., PNAS (USA) 82: 4673-4677, 1985, herein incorporated by reference).

Phage DNA was prepared from positive clones by the method of Silhavy et al. (Experiments with Gene Fusion, Cold Spring Harbor Laboratory, 1984). The purified phage DNA was digested with EcoRI and subcloned into pUC9 for further mapping and sequencing studies. Further analysis suggested that the gene for protein C was present in three EcoRI fragments. In order to generate overlapping protein C DNA sequences, purified phage DNA was digested with Bgl II and subcloned into pUC9.

The sequences of the EcoRI and Bgl II protein C fragments were determined by subcloning the fragments into M13 phage cloning vectors. Sequence analysis of the overlapping fragments established the DNA sequence of the entire protein C gene.

Alternatively, the complete DNA sequence has been determined using a second cDNA clone isolated from a λgt11 cDNA library. This clone encodes a major portion of protein C, beginning at amino acid 24 and including the heavy chain coding region, termination codon, and 3' noncoding region. The insert from this λ phage clone was subcloned into pUC9 and the resultant plasmid designated pHC 6L.

This pHC 6L insert was nick translated and used to probe a human genomic library in phage λ Charon 4A. One genomic clone was identified which contained a 4.4 kb EcoRI fragment corresponding to the 5' end of the protein C gene. This phage clone was subcloned into pUC9 and the resultant plasmid designated pHCR 4.4. DNA sequence analysis revealed that the pHCR 4.4 insert comprised two exons, encoding amino acids −42 to −19, and amino acids −19 to 37. Thus, the DNA sequence of the entire protein C gene was established due to the overlapping sequences of pHC 6L (24 to 3' noncoding region) and pHCR 4.4 (−42 to 37).

From the foregoing it will be appreciated that, although specific embodiments of the invention have been described herein for purposes of illustration, various modifications may be made without deviating from the spirit and scope of the invention. Accordingly, the invention is not limited except as by the appended claims.

Claims:

1. An isolated DNA sequence encoding the heavy chain of human protein C.

2. An isolated DNA sequence encoding human protein C from amino acid No. 64 to amino acid No. 419, as shown in FIG. 3.

* * * * *

UNITED STATES PATENT AND TRADEMARK OFFICE
CERTIFICATE OF CORRECTION

PATENT NO : 5,073,609
DATED : Dec. 17, 1991
INVENTOR(S) : Donald C. Foster, Earl W. Davie It is certified that error appears in the above-identified patent and that said Letters Patent are hereby corrected as shown below:

At column 1 following the title, please add the following:

--GOVERNMENT SUPPORT

This invention was made with government support under National Institutes of Health grant number HL16919. The government has certain rights in the invention.--

Signed and Sealed this

Eighth Day of May, 2001

NICHOLAS P. GODICI

*Attest:*

*Attesting Officer*      *Acting Director of the United States Patent and Trademark Office*